(12) United States Patent
Tsukashima et al.

(10) Patent No.: US 12,102,778 B2
(45) Date of Patent: Oct. 1, 2024

(54) ELECTRICALLY-RESPONSIVE HYDROGELS

(71) Applicant: MicroVention, Inc., Aliso Viejo, CA (US)

(72) Inventors: Ross Tsukashima, Aliso Viejo, CA (US); Heath Bowman, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 511 days.

(21) Appl. No.: 17/453,801

(22) Filed: Nov. 5, 2021

(65) Prior Publication Data
US 2022/0054801 A1 Feb. 24, 2022

Related U.S. Application Data

(63) Continuation of application No. 16/277,995, filed on Feb. 15, 2019, now Pat. No. 11,191,925, which is a
(Continued)

(51) Int. Cl.
*A61M 25/01* (2006.01)
*A61B 17/12* (2006.01)
(Continued)

(52) U.S. Cl.
CPC ... *A61M 25/0158* (2013.01); *A61B 17/12113* (2013.01); *A61B 17/12145* (2013.01); *A61B 17/1215* (2013.01); *A61B 17/1219* (2013.01); *A61B 17/22* (2013.01); *A61B 17/22031* (2013.01); *A61L 29/14* (2013.01); *A61L 29/145* (2013.01); *A61M 11/006* (2014.02); *A61M 13/00* (2013.01); *A61M 13/003* (2013.01); *A61M 16/0459* (2014.02); *A61M 16/0463* (2013.01); *A61M 16/0486* (2014.02); *A61M 25/0043* (2013.01); *A61M 25/04* (2013.01); *A61B 2017/00154* (2013.01);
(Continued)

(58) Field of Classification Search
CPC ........ A61B 17/12113; A61B 17/12145; A61B 17/1215; A61B 17/1219; A61B 17/22; A61B 17/22031; A61B 2017/00871; A61B 2017/00154; A61B 2017/00898; A61B 2017/1209; A61L 29/14; A61L 29/145; A61M 11/006; A61M 13/00; A61M 13/003; A61M 16/0459; A61M 16/0463; A61M 16/0486; A61M 2025/0058; A61M 25/0043; A61M 25/0158; A61M 25/04; A61M 2205/3306; A61M 2210/1032; A61M 2210/105; A61M 2210/1053; A61M 2210/1085
See application file for complete search history.

(56) References Cited

U.S. PATENT DOCUMENTS 5,976,131 A 11/1999 Guglielmi et al.
6,478,774 B1 11/2002 Balugani et al.
(Continued)

*Primary Examiner* — Jason E Flick
(74) *Attorney, Agent, or Firm* — Inskeep IP Group, Inc.

(57) ABSTRACT

Implants comprising electrically-responsive hydrogel are described. Systems to provide electricity to induce response in hydrogel-containing implants are described. Methods for utilizing said system and methods for utilizing said hydrogel-containing implants are described.

19 Claims, 14 Drawing Sheets

Related U.S. Application Data continuation of application No. 14/549,514, filed on Nov. 20, 2014, now Pat. No. 10,232,144.

(60) Provisional application No. 61/919,637, filed on Dec. 20, 2013.

(51) Int. Cl.
| | |
|---|---|
| *A61B 17/22* | (2006.01) |
| *A61L 29/14* | (2006.01) |
| *A61M 11/00* | (2006.01) |
| *A61M 13/00* | (2006.01) |
| *A61M 16/04* | (2006.01) |
| *A61M 25/00* | (2006.01) |
| *A61M 25/04* | (2006.01) |
| *A61B 17/00* | (2006.01) |

(52) U.S. Cl.
CPC ............ *A61B 2017/00871* (2013.01); *A61B 2017/00898* (2013.01); *A61B 2017/1209* (2013.01); *A61M 2025/0058* (2013.01); *A61M 2205/3306* (2013.01); *A61M 2210/1032* (2013.01); *A61M 2210/105* (2013.01); *A61M 2210/1053* (2013.01); *A61M 2210/1085* (2013.01)

(56) References Cited

U.S. PATENT DOCUMENTS

| | | |
|---|---|---|
| 6,620,152 B2 | 9/2003 | Guglielmi |
| 2011/0184455 A1* | 7/2011 | Keeley ............ A61B 17/12145 |
| | | 606/200 |
| 2011/0301686 A1 | 12/2011 | Bowman et al. |
| 2012/0101456 A1 | 4/2012 | Forsell |
| 2013/0023850 A1 | 1/2013 | Imran et al. |
| 2013/0131711 A1 | 5/2013 | Bowman |
| 2013/0245606 A1* | 9/2013 | Stam ................. A61B 17/1219 |
| | | 264/41 |

* cited by examiner

ELECTRICALLY-RESPONSIVE HYDROGELS

RELATED APPLICATIONS

This application is a continuation of and claims priority to U.S. patent application Ser. No. 16/277,995 filed Feb. 15, 2019 entitled Electrically-Responsive Hydrogels, which is a continuation of and claims priority to U.S. patent application Ser. No. 14/549,514 filed Nov. 20, 2014 entitled Electrically-Responsive Hydrogels (now U.S. Pat. No. 10,232,144 issued Mar. 19, 2019), which claims benefit of and priority to U.S. Provisional Application Ser. No. 61/919,637 filed Dec. 20, 2013 entitled Electrically-Responsive Hydrogels, all of which are hereby incorporated herein by reference in their entireties.

BACKGROUND OF THE INVENTION

Vessel occlusion is often necessary in a variety of cases including but not limited to treatment of aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature. One method of treatment involves insertion of an expansile material, such as hydrogel, for occlusion. Hydrogel is an expansile, hydrophilic polymer. Hydrogel can be incorporated in embolization coils or can be injected independently. Hydrogel typically expands when exposed to material, such as blood. This response is based on the pH of the material the hydrogel is exposed to. The hydrogel or hydrogel-containing implant has a contracted form during deployment, and adopts an expanded form suitable for occlusive purposes after exposure to blood. During interventional procedures, the working time for introducing and deploying hydrogel or a hydrogel-containing implant is relatively low due to its expansile properties. A method of controlling hydrogel expansion would thus be beneficial to extend working time during interventional procedures. Alternatively, a method of augmenting hydrogel expansion would be beneficial to enhance the space filling properties of the hydrogel or hydrogel-containing implant.

Broadly, a system and/or method to control contraction and/or expansion of a hydrogel could aid in interventional procedures.

SUMMARY OF THE INVENTION

In one embodiment an implant utilizing an electrically-responsive hydrogel is described.

In another embodiment a system used to control an electrically-responsive hydrogel is described.

In another embodiment a method of controlling an electrically-responsive hydrogel is described.

In another embodiment a method of utilizing an electrically-responsive hydrogel is described.

In another embodiment a method of utilizing an implant comprising an electrically-responsive hydrogel is described.

In another embodiment a drug delivery device utilizing an electrically-responsive hydrogel is described.

In another embodiment a steerable catheter utilizing an electrically-responsive hydrogel is described.

In another embodiment a liquid embolic delivery catheter utilizing an electrically-responsive hydrogel is described.

In another embodiment an intrasaccular occlusion device utilizing an electrically-responsive hydrogel is described.

In another embodiment a stroke treatment device utilizing an electrically-responsive hydrogel is described.

In another embodiment an anchor utilizing an electrically-responsive hydrogel is described.

DETAILED DESCRIPTION

Hydrogels may expand or contract based on electric impulse, see Collapse of Gels in an Electric Field, Science Vol. 218 pgs 467-469, Flow control with hydrogels, Advanced Drug Delivery Reviews 56 (2004) 199-210, Electro-responsive drug delivery from hydrogels, Journal of Controlled Release 92 (2003) 1-7 all of which are hereby incorporated by reference in their entirety.

Generally, hydrogels used for interventional procedures (e.g., filling aneurysms) expand on contact with blood.

A sufficiently high positive charge applied to a hydrogel results in one of two scenarios. In one scenario the hydrogel will shrink or contract. In another scenario the hydrogel either will not expand or will not expand as much as it would otherwise expand when exposed to blood or another material of a comparable pH level. That is, the hydrogel will be prone to expand when exposed to blood, yet the contracting action provided by the positive charge will cause the hydrogel to expand less than it would otherwise.

During interventional procedures, procedure time is important since a lengthy procedure time may result in expansion of the hydrogel, making deployment of the hydrogel or hydrogel-containing implant difficult. For example, if blood enters the delivery device (e.g., catheter) that the hydrogel or hydrogel-containing implant is delivered through the blood may react with the hydrogel causing expansion of the hydrogel and resulting in increased friction when pushing the hydrogel or hydrogel-containing implant through the delivery device. A positive charge applied to the hydrogel during deployment would either shrink the hydrogel or mitigate expansion of the hydrogel when exposed to blood during deployment, thus increasing workable interventional procedure times.

Contrarily, a sufficiently high negative charge applied to a hydrogel tends to cause the hydrogel to expand or bulge. This property can be used to further enhance the space filling potential of a hydrogel or hydrogel-containing implant.

Figure 10:
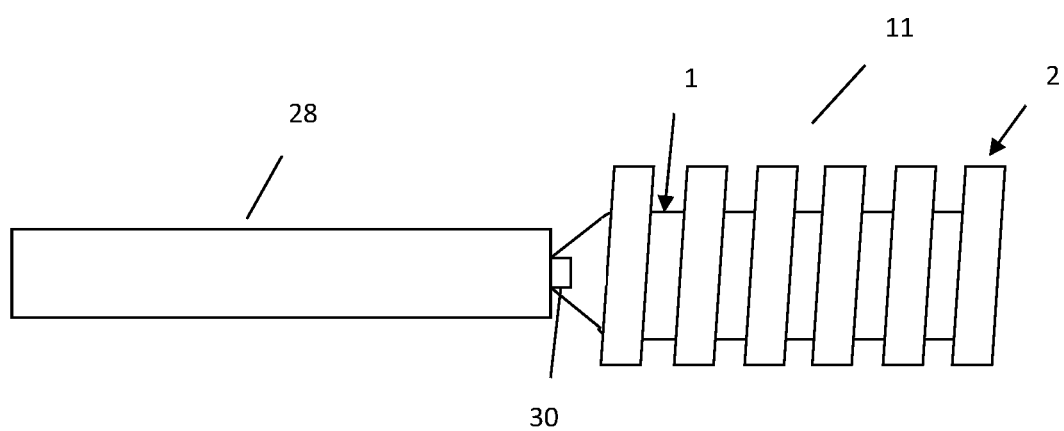
FIG. 10 illustrates the junction of the core wire and hydrogel-containing implant.

Please note for reference of the description provided the terms "proximal" and "distal" will generally be used relative to the position of the implant within the vasculature. Thus the term "distal" will refer to a more downstream facing position whereas the term "proximal" will refer to a more upstream facing position. In this context, utilizing FIG. 1 as an example, tip 4 sits distal of coupler 13. Referring to FIG. 10 as another example, core wire 28 sits proximal relative to implant 11 and implant 11 sits distal relative to core wire 28.

Figure 1:
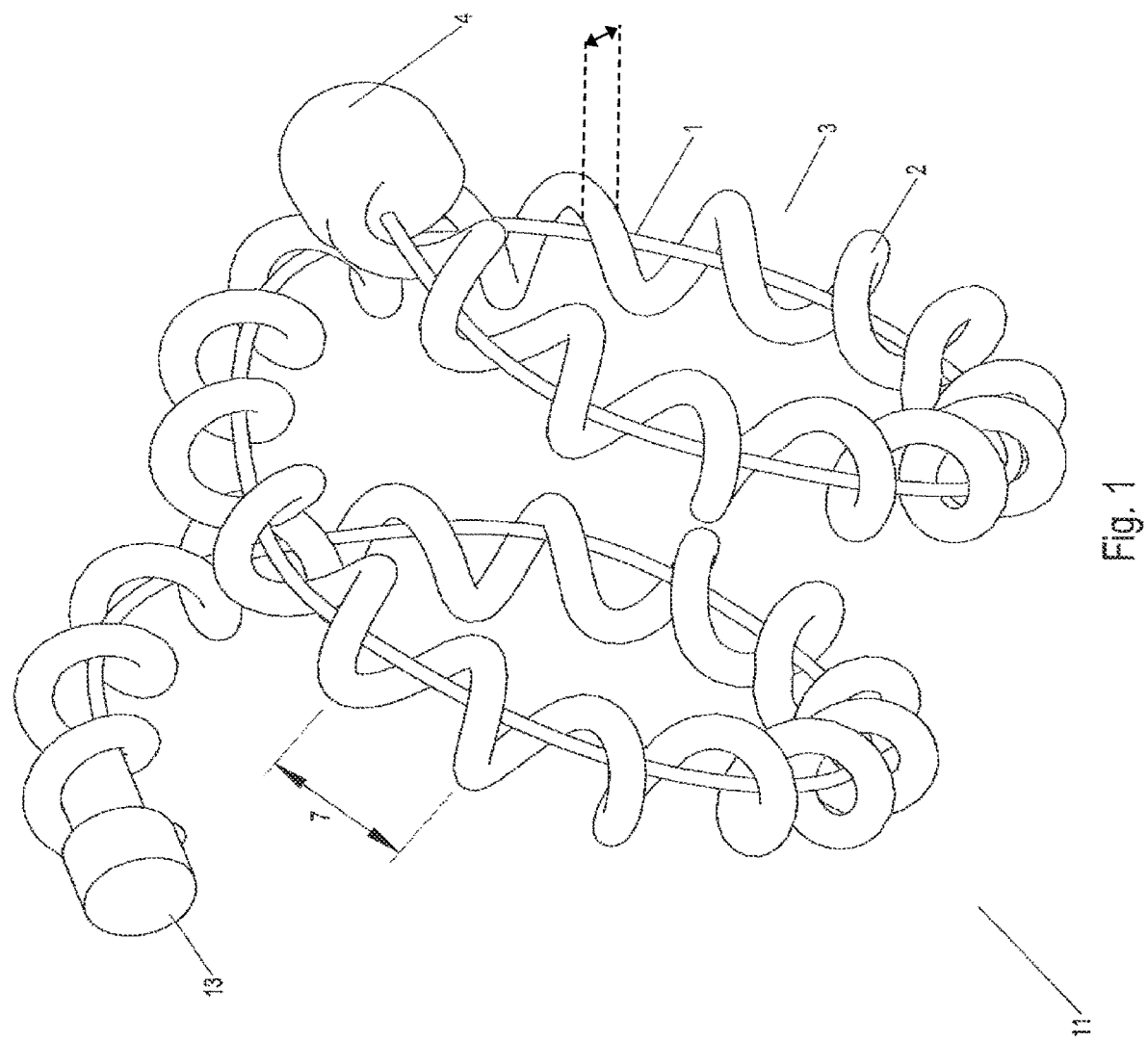
FIG. 1 illustrates an implant utilizing a hydrogel where said implant is in a contracted state.
Figure 3:
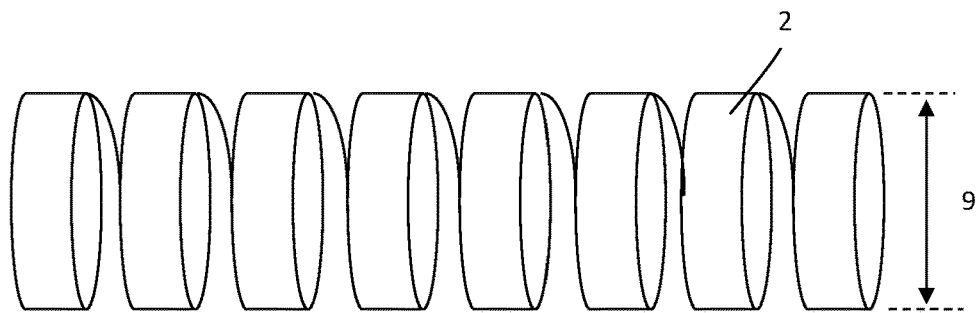
FIGS. 3-5 illustrate an implant utilizing a hydrogel, where said implant progresses from a contracted through an expanded state.
Figure 4:
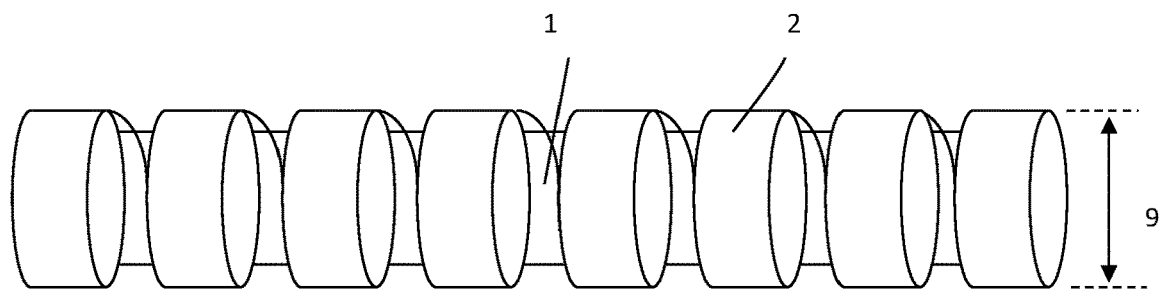
Figure 5:
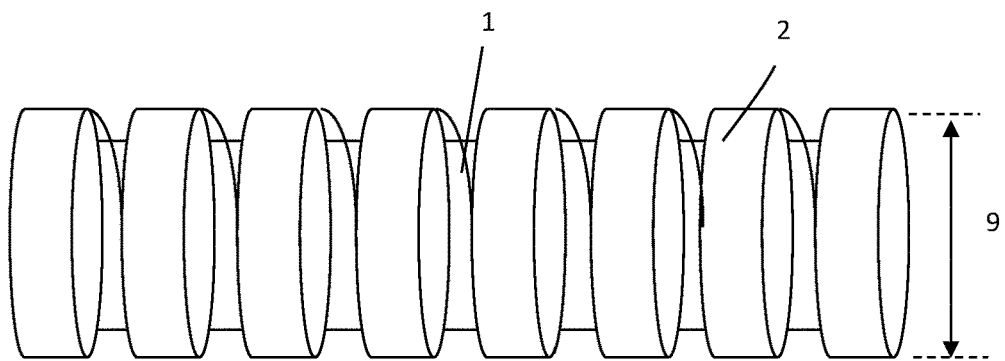

FIG. 1 illustrates an implant 11 comprising a carrier 2 and hydrogel 1 disposed within a lumen 3 of the carrier 2. Carrier 2 contains at least one gap 7. The carrier, as an example, could be a helically wound coil comprised of a metallic or polymeric material. Carrier 2 has a thickness 8 and a diameter 9. Diameter 9 is shown in FIGS. 3-5. A tip 4 may be formed at the distal end of implant 11 by, for example, a laser, solder, adhesive, or melting the hydrogel material itself. Alternatively the tip could be the same material as the carrier. A coupler 13 sits at the proximal end of implant 11 and is connected to a delivery system. In one example a degradable electrolytic, thermal, or mechanical linkage is connected to coupler 13 to sever implant 11 from the delivery system. In another example coupler 13 is itself degradable by electrolytic, thermal, or mechanical means to sever implant 11 from the delivery system. One such thermal detachment system that could be used is shown in U.S. Pat. No. 8,182,506 and U.S. Publication No. 2006/0200192, which are hereby incorporated by reference in their entirety. Another detachment system that could be used is shown in U.S. Pat. No. 6,620,152, which is hereby incorporated by reference in its entirety.

FIG. 1 is offered as an example configuration for a hydrogel-containing implant. Other configurations could utilize hydrogel coating on the outside of a coil or carrier member, hydrogel placed within a slotted tube/carrier member, hydrogel alone, or other possible configurations.

Figure 2:
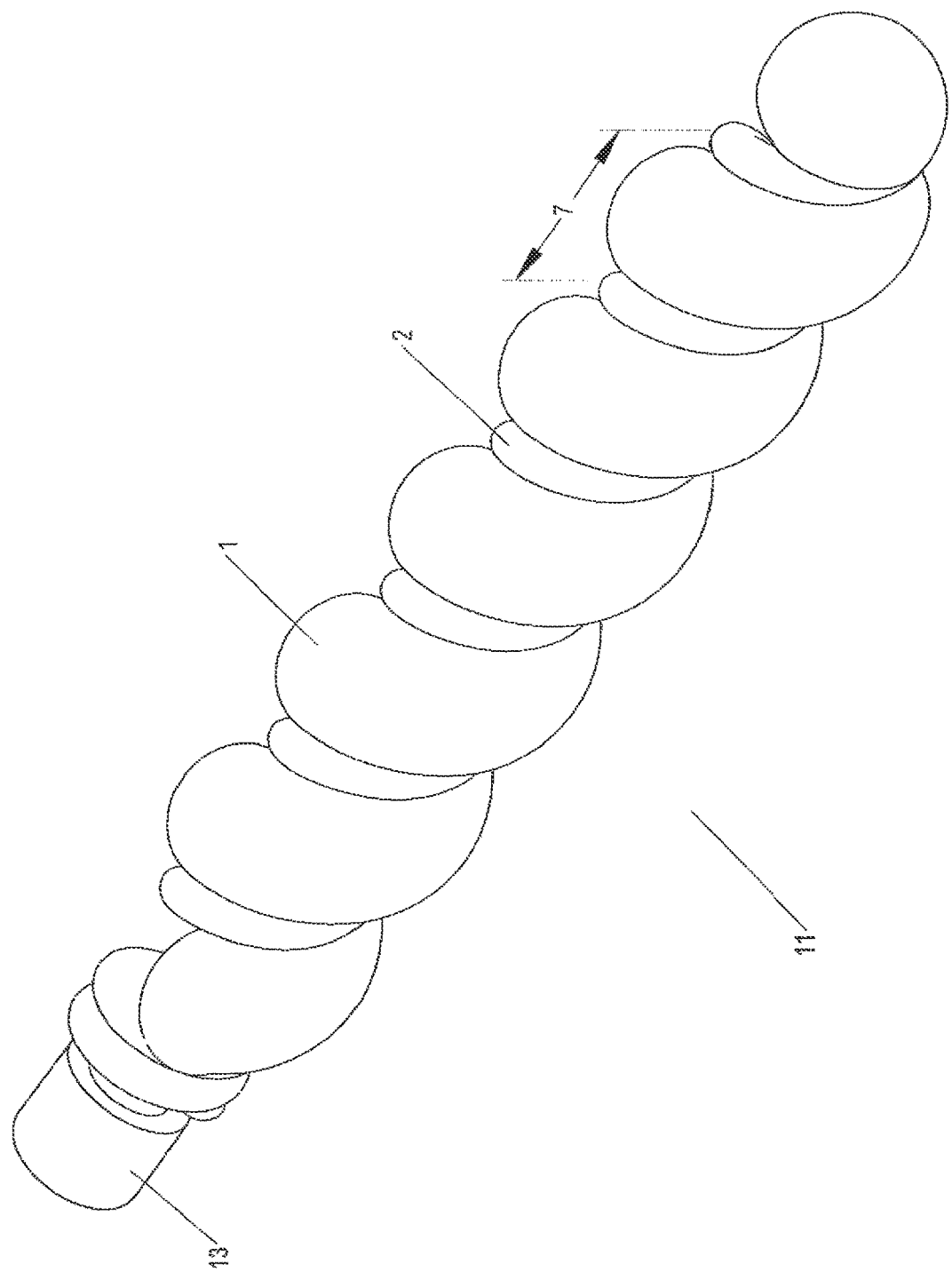
FIG. 2 illustrates an implant utilizing a hydrogel where said implant is in an expanded state.

FIG. 2 illustrates implant 11 from FIG. 1 with hydrogel 1 expanded. In some implant configurations the hydrogel may expand beyond carrier diameter 9 through gap 7, as shown in FIG. 2. Alternatively, in other implant configurations the hydrogel may expand to the periphery carrier diameter 9 or to a point within the periphery of carrier diameter 9. The expansile properties of the hydrogel, carrier diameter, carrier width, and tensile properties of the constituent carrier material are all properties which can affect the amount of hydrogel expansion relative to the carrier.

Hydrogel utilized for intravascular therapeutic applications (e.g., filling an aneurysm) is typically designed to expand when exposed to blood to enhance space filling potential of the implant. If blood enters the catheter and reacts with the hydrogel, the hydrogel may expand prematurely making tracking of the hydrogel-containing implant through the catheter or delivery device difficult. This is especially true for the implant shown in FIGS. 1-2, where hydrogel 1 can expand beyond carrier diameter 9. In another scenario, when placing the hydrogel-containing implant in the target treatment site, it may be desirable to move the implant around prior to the hydrogel expanding to make sure the implant is in the correct location within the treatment site. The natural expansion of hydrogel upon contact with blood limits the time available to do so.

Another implant configuration could utilize hydrogel placed within a carrier with a tighter winding (i.e. a smaller gap 7) than what is shown in FIG. 1. In such a configuration the hydrogel would expand and push on the carrier, thus expanding the diameter of the carrier. As a result the hydrogel may not necessarily expand through the lumen of the carrier as shown in FIG. 2. Instead as the hydrogel expands it would push on the carrier, resulting in the radial expansion of the carrier. Another implant configuration could utilize a greater carrier thickness 8. The thicker carrier would limit the ability of hydrogel to seep through the lumen of the carrier as the hydrogel expands and thus utilize the expansion of the hydrogel to, in turn, assist the radial expansion of the carrier. In one example the carrier is heat-set to an initial shape. The hydrogel is affixed within the carrier and is stretched into tension. The stretching of the hydrogel causes the carrier to also stretch. The diameter of the carrier windings effectively decreases as the carrier stretches. When the hydrogel is exposed to blood and expands the hydrogel will, in turn, push on the carrier. This causes the carrier to radially expand and assume a shape closer to its initial, pre-tensioned diameter. This is shown in FIGS. 3-5.

FIG. 3 shows the initial shape of carrier 2. In FIG. 4 hydrogel 1 is secured to carrier 2 and put in tension, causing carrier 2 to also stretch, thus decreasing diameter 9. In FIG. 5 hydrogel 1 swells due to contact with blood, causing an expansion in diameter 9.

The tendency of hydrogel to contract upon exposure to a positive charge and expand upon exposure to a negative charge can be useful for a variety of purposes. In a scenario described earlier, blood may enter the delivery device causing premature expansion of the hydrogel during delivery of the hydrogel-containing implant. Applying an appropriately significant positive charge to the hydrogel will shrink the hydrogel or limit its expansion upon contact with blood, thus allowing easier movement of the hydrogel-containing implant through the delivery device. The principle described above (applying an appropriately significant positive charge to the hydrogel thus limiting its expansion) will also help in a scenario described earlier involving placement of a hydrogel-containing implant within the vasculature. An appropriately significant positive charge can be applied to the hydrogel to limit its expansion upon contact with blood. Once the implant is placed appropriately, the positive charge can be removed allowing the hydrogel to expand and fill the region. Alternatively, once the implant is placed appropriately a negative charge can be applied to the hydrogel to augment its expansion, further enhancing the space filling capability of the hydrogel and/or hydrogel-containing implant.

Figure 6:
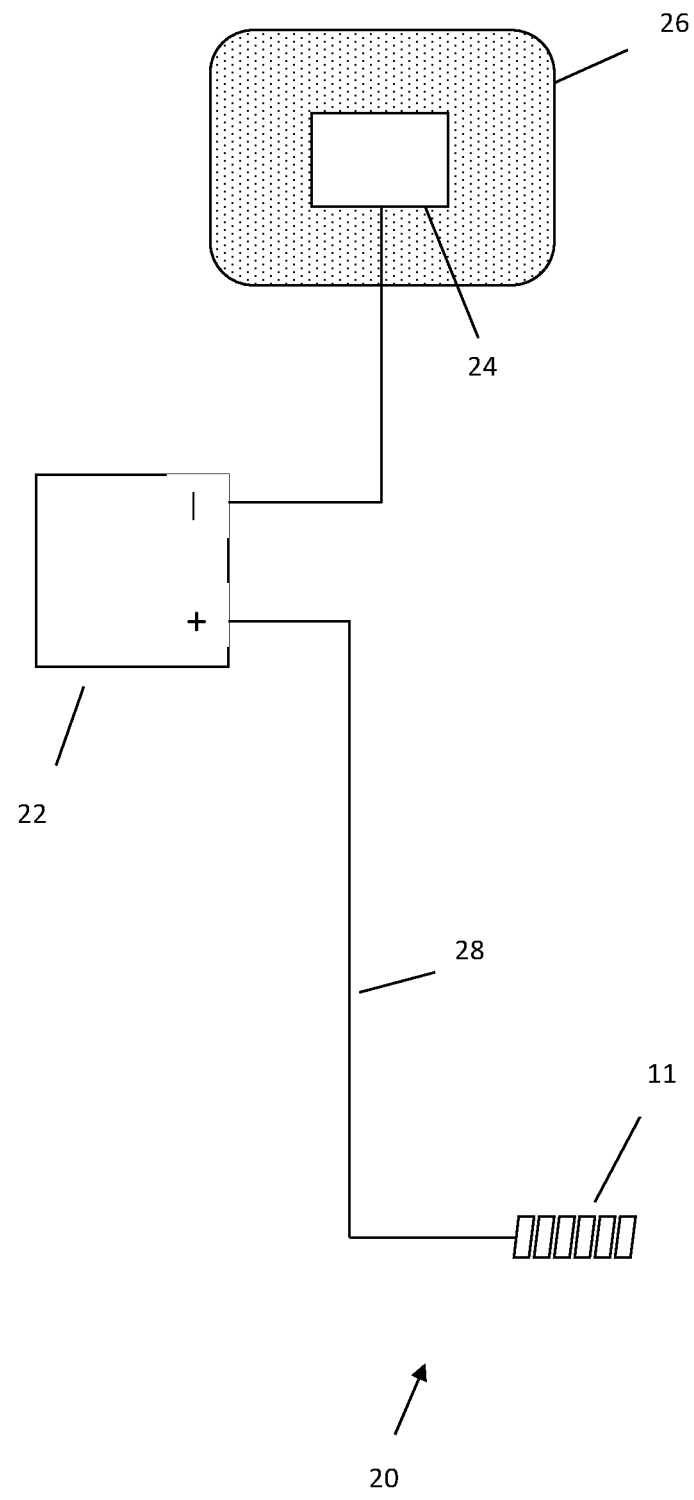
FIG. 6 illustrates a system used to mitigate expansion of hydrogel in an implant.

FIG. 6 illustrates a system 20 to mitigate hydrogel expansion. The system includes a battery or voltage source 22. The configuration shown in FIG. 6 would be used to contract or prevent/limit expansion of the hydrogel by connecting the positive terminal of the voltage source to the implant. The negative terminal of the voltage source is connected to the skin 26 of the patient via a patient node, which, in one embodiment is a patch 24. The current runs from the positive terminal of voltage source 22 to core wire 28 to the hydrogel within hydrogel-containing implant 11, through the ionic solution within the body, through patch 24 and back to the negative terminal of voltage source 22.

Figure 7:
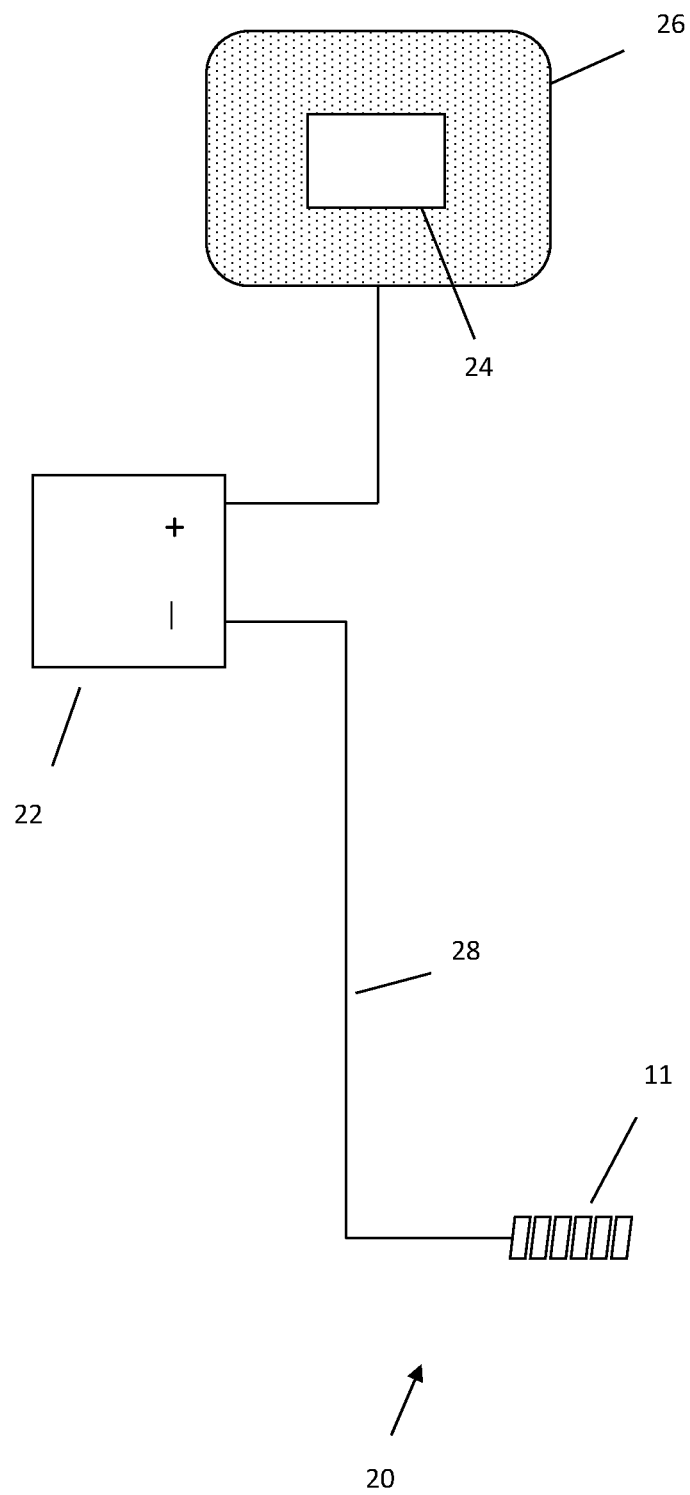
FIG. 7 illustrates a system used to augment expansion of hydrogel in an implant.

FIG. 7 illustrates a system 20 used to augment hydrogel expansion. In this system the negative terminal of the voltage source is connected to hydrogel 1 via core wire 28. The current in this system would run from the positive terminal of the voltage source through patch 24, through skin 26, through the ionic solution within the body, through hydrogel 1, through core wire 28 and to the negative terminal of the voltage source.

In the systems shown in FIG. 6 and FIG. 7 the wires which connect to the positive and negative terminals of voltage source 22 may be switched to change the polarity of the system, thus alternating between expansion and contraction of the hydrogel.

Figure 8:
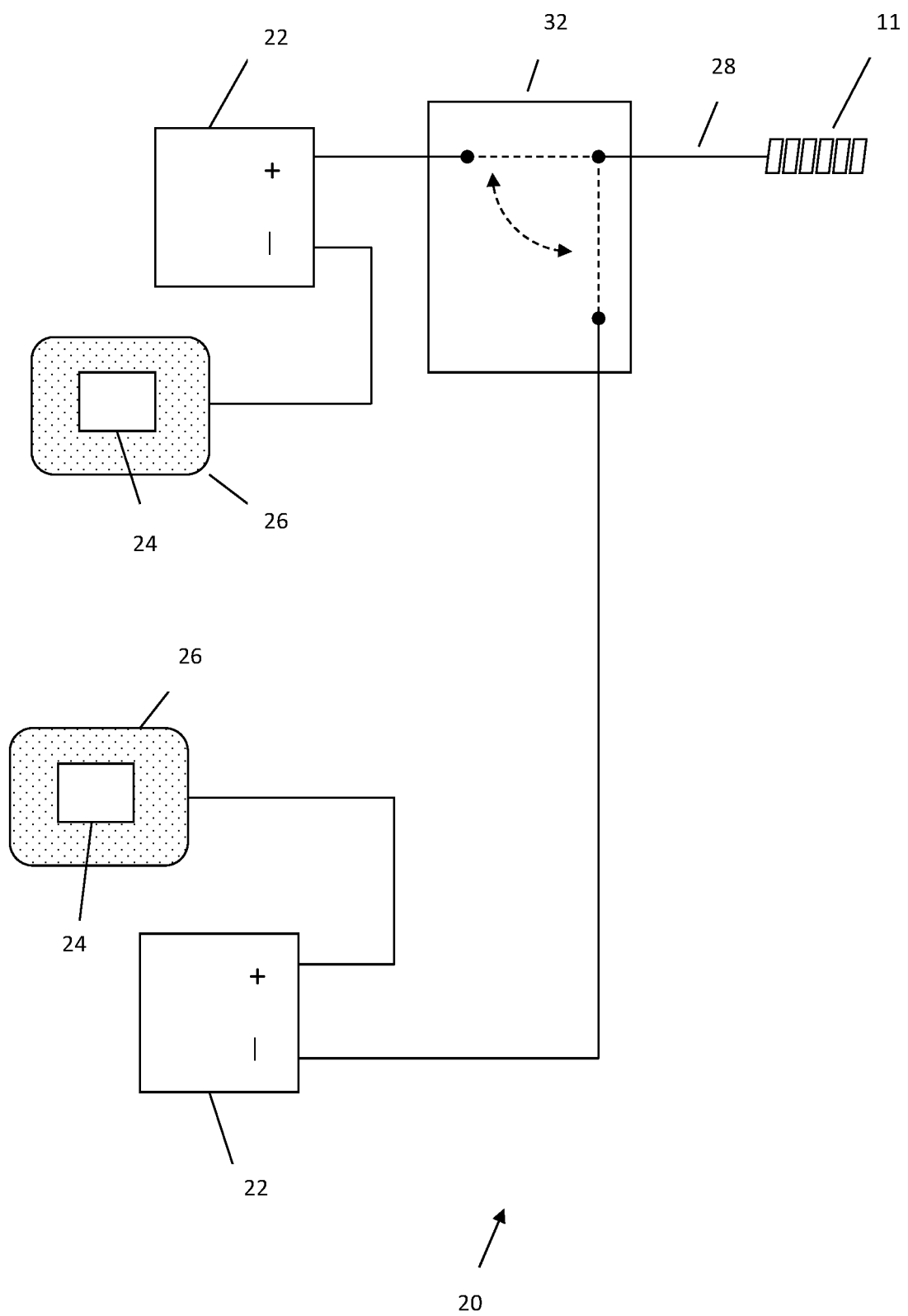
FIG. 8 illustrates a system used to selectively either mitigate or augment expansion of hydrogel in an implant.

In another embodiment shown in FIG. 8 the systems shown in FIGS. 6 and 7 may be combined in one system 20 utilizing two separate voltage sources. One circuit would have the configuration shown in FIG. 6 with one voltage source, another circuit would utilize the configuration shown in FIG. 7 with another voltage source. A user could utilize a switch 32 to switch between the two systems to either apply a positive or a negative charge to the hydrogel. Switch 32 could be coupled to a user interface, where the user could interact with the interface to control the switch position. In one example the positive terminal of one voltage source and the negative terminal of the other voltage source could be connected to the same patch.

Figure 9:
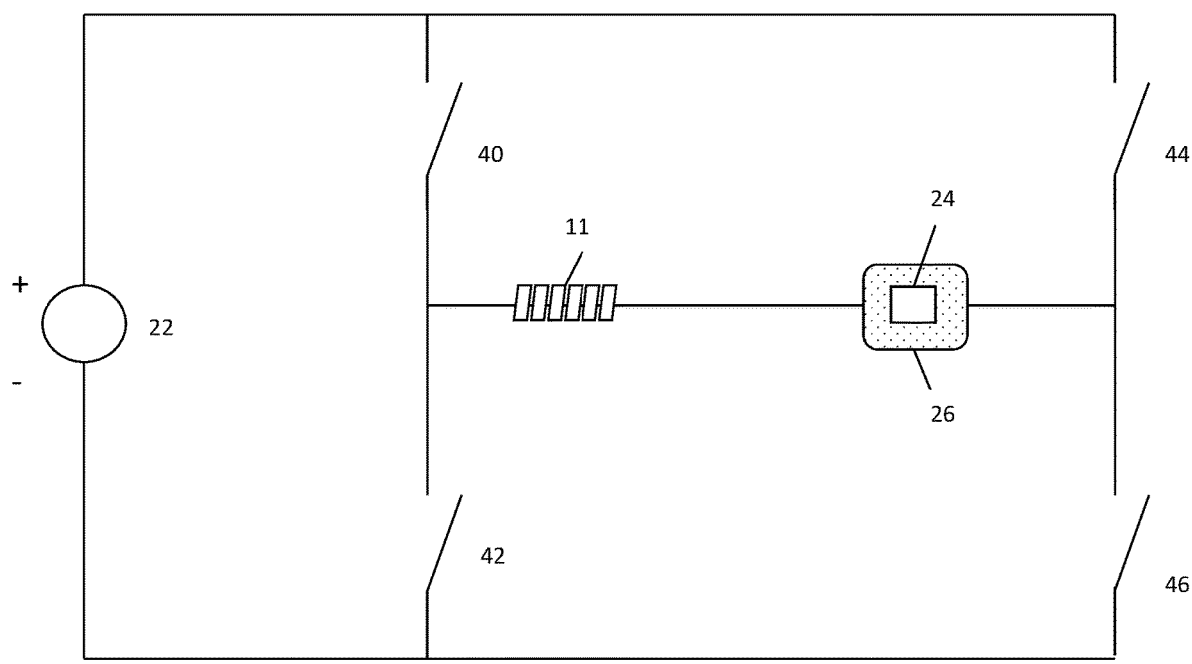
FIGS. 9, 9a, 9b illustrate a system used to selectively either mitigate or augment expansion of hydrogel in an implant, where said system utilizes one voltage source.

In another embodiment, a single voltage source can utilize an H-bridge to cause either a positive or negative charge to be applied to the hydrogel. H-bridges can be used in a circuit to vary the flow path within the circuit. The circuit utilizing the H-bridge can be coupled to a user interface to control the flow path. In one position a positive charge can be delivered to the hydrogel-containing implant, whereas in another position a negative charge can be delivered to the hydrogel-containing implant thus resulting in either contraction or expansion of the hydrogel. FIG. 9 illustrates an H-bridge circuit design.

Figure 9A:
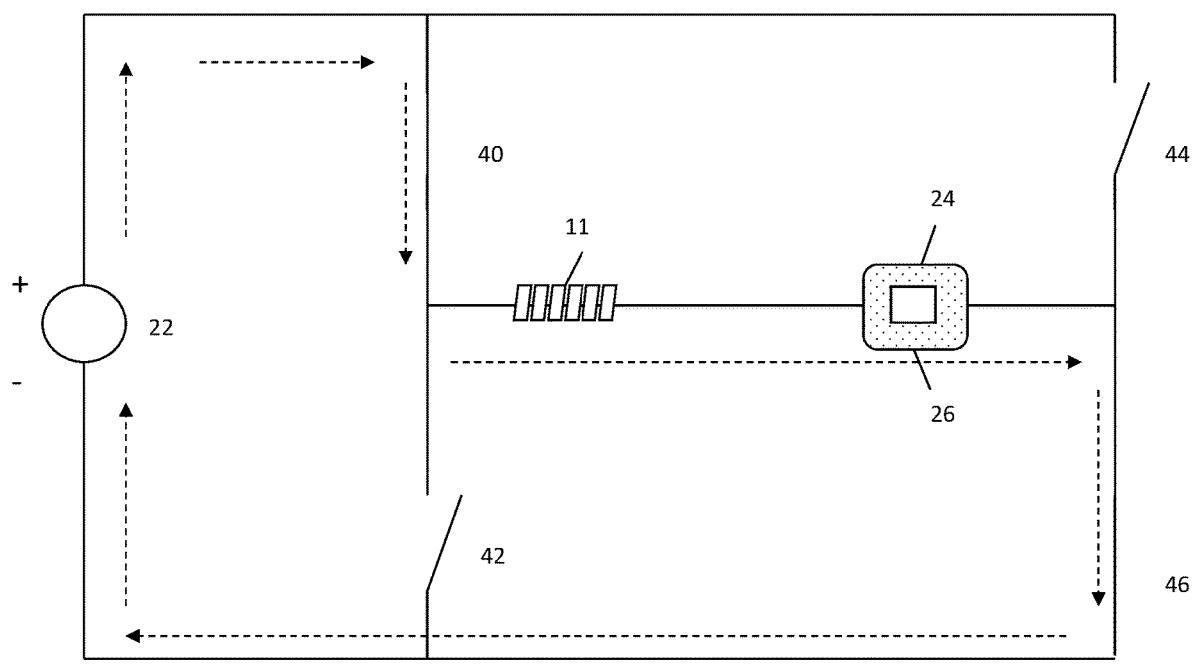

In FIG. 9a switches 40 and 46 are closed while switches 42 and 44 remain open. In this configuration current is delivered first through the hydrogel, through the body ionic content, through the skin patch, then back to the voltage source. In this manner a positive charge is applied to the hydrogel thus resulting in contraction or limited expansion of the hydrogel.

Figure 9B:
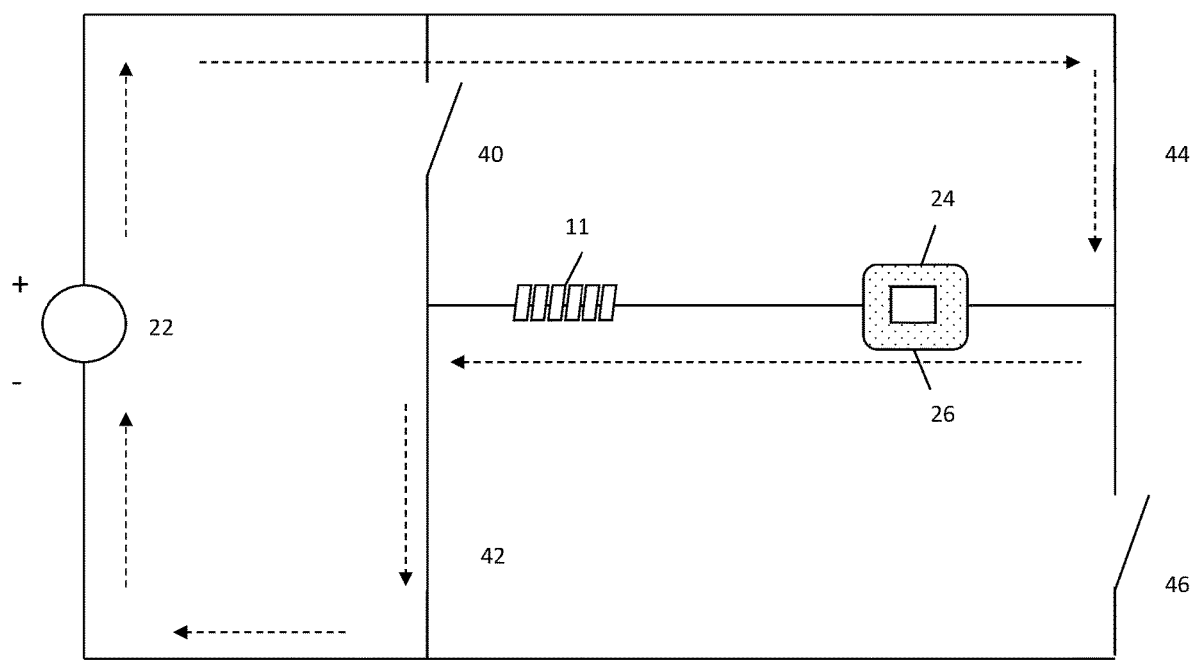

In FIG. 9b switches 42 and 44 are closed while switches 40 and 46 remain open thus resulting in current flow through the skin patch, through the body ionic content, through the hydrogel, then back to the voltage source. In this manner a negative charge is applied to the hydrogel thus resulting in expansion of the hydrogel. An interface can be coupled to the H-bridge circuit to allow the user to apply a positive or negative charge to the hydrogel during the interventional procedure.

FIG. 10 illustrates the core wire-hydrogel connection. Core wire 28 can be made of a conductive material to transfer the charge from voltage source 22 to hydrogel 1. A separate wire may connect between the terminal of voltage source 22 and a proximal part of core wire 28 to establish the current flow between the voltage source and core wire. The hydrogel is connected to core wire 28 to receive the charge. A degradable electrolytic, thermal, or mechanical linkage 30 may be connected to core wire 28, and run between the core wire and implant 11. The linkage 30 may also be conductive in order to transfer the charge to the hydrogel. The degradation of linkage 30 would detach implant 11 from core wire 28.

In another embodiment, instead of core wire 28 being conductive, one or more wires can connect the voltage source 22 and hydrogel 1. Alternatively, wires can connect voltage source 22 to a distal part of core wire 28 where said distal part of core wire 28 is conductive to carry the charge between voltage source 22 and hydrogel 1 which is attached to said distal part of core wire 28.

In an alternative embodiment an alternating current (AC) voltage source can be used instead of the DC sources shown and described earlier.

Figure 11:
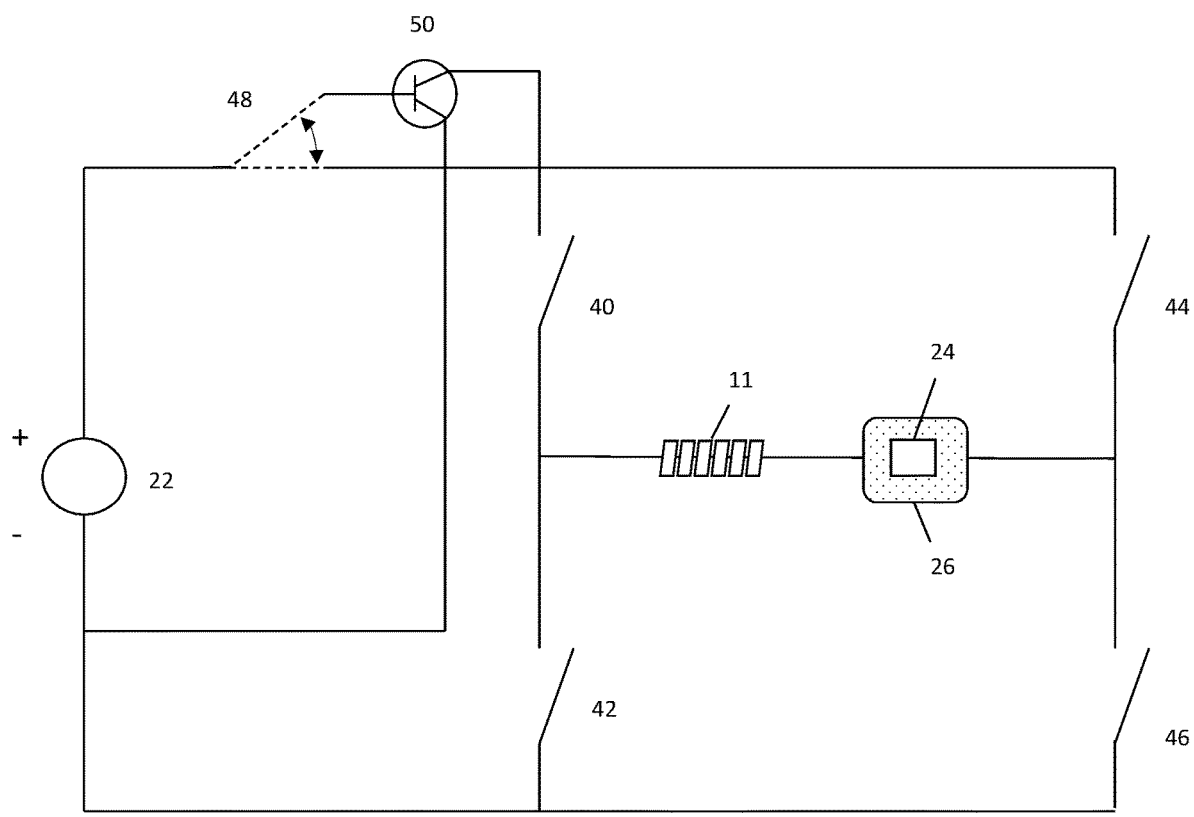
FIGS. 11, 11a-11c illustrates a system used to both a) selectively either mitigate or augment expansion of hydrogel in an implant and b) detach the hydrogel-containing implant.

Pulse width modulation or other techniques can be used to deliver the voltage from the voltage source to the hydrogel. Pulse width modulation would deliver voltage as a spaced waveform instead of as a constant load. Pulse width modulation could reduce potential bubbling of the ionic content within the body by spacing the voltage delivered through the body, instead of delivering a constant load. The use of pulse-width modulation can be used in a combined system utilizing one or more voltage sources. This combined system could both polarize the hydrogel and detach the implant. An example of such a system is shown in FIG. 11. FIG. 11 illustrates the outline for the system while FIGS. 11a-11c illustrate possible switch positions and how the current moves through the system based on the various switch positions.

FIG. 11 includes a switch 48 which either connects a portion of the circuit (in its lower position) or a transistor 50 (in its upper position). The transistor may provide the pulse width modulation. In the example shown in the Figures pulse width modulation is used to polarize the hydrogel and the direct current is used to detach the implant. However, this can be switched around if desired so that pulse-width is used to detach the implant and the direct current is used to polarize the hydrogel. Variables such as the response of the hydrogel to electric impulse and the material properties of linkage 30 may be useful to determine whether direct or pulse-width modified techniques are suitable for each purpose.

Figure 11A:
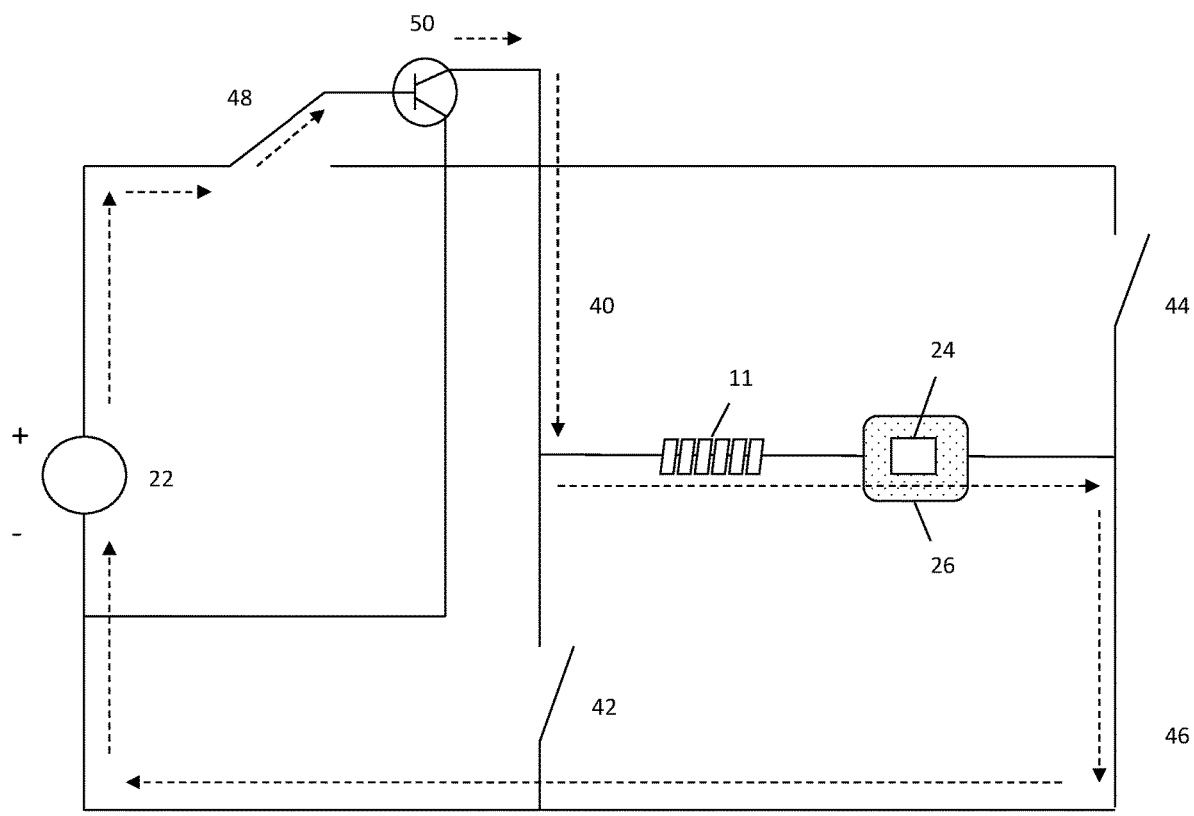

FIG. 11a illustrates a system utilizing pulse width modulation to apply a positive charge to the hydrogel. Switch 48 in its upper position sends current through transistor 50, transistor 50 may alter the signal from voltage source 22, for example, by providing pulse width modulation. The current then travels through the hydrogel, through the ionic content of the body, through the skin patch, then back to the negative terminal of the voltage source. This flow path is due to switches 40 and 46 being closed.

Figure 11B:
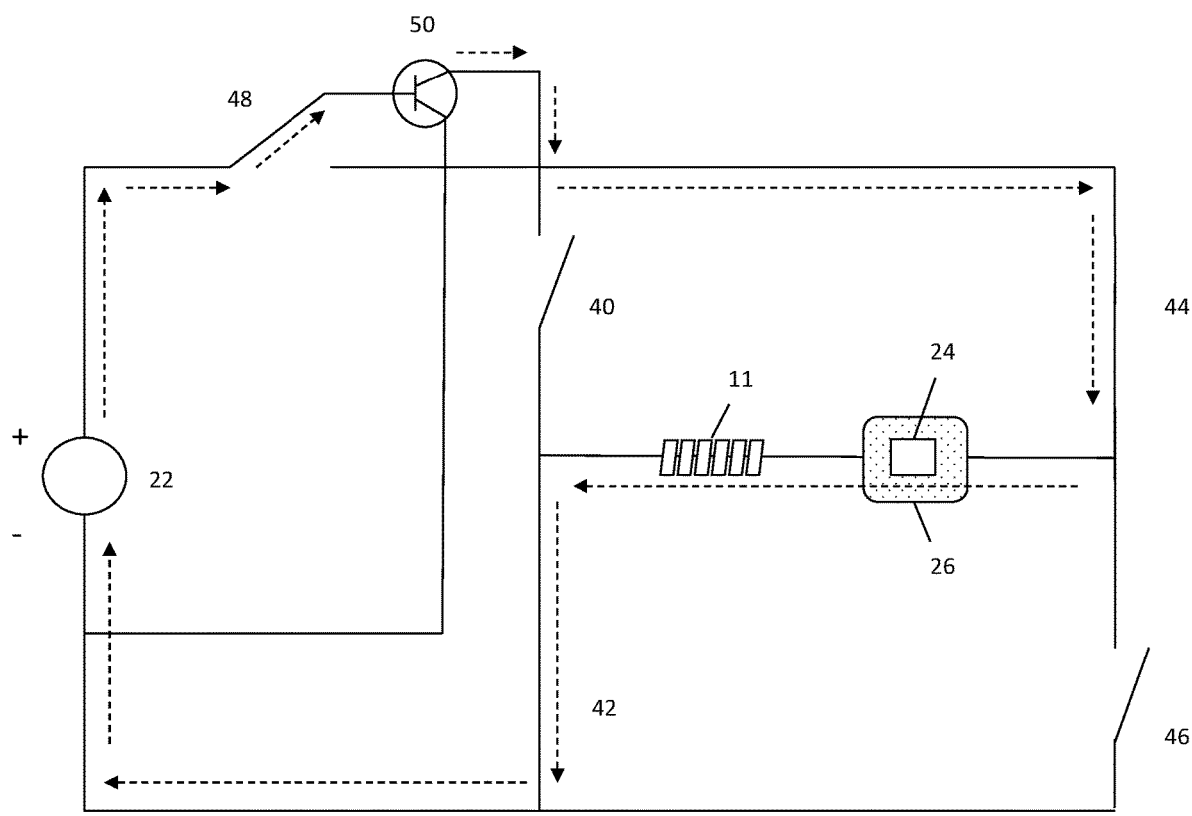
Figure 11C:
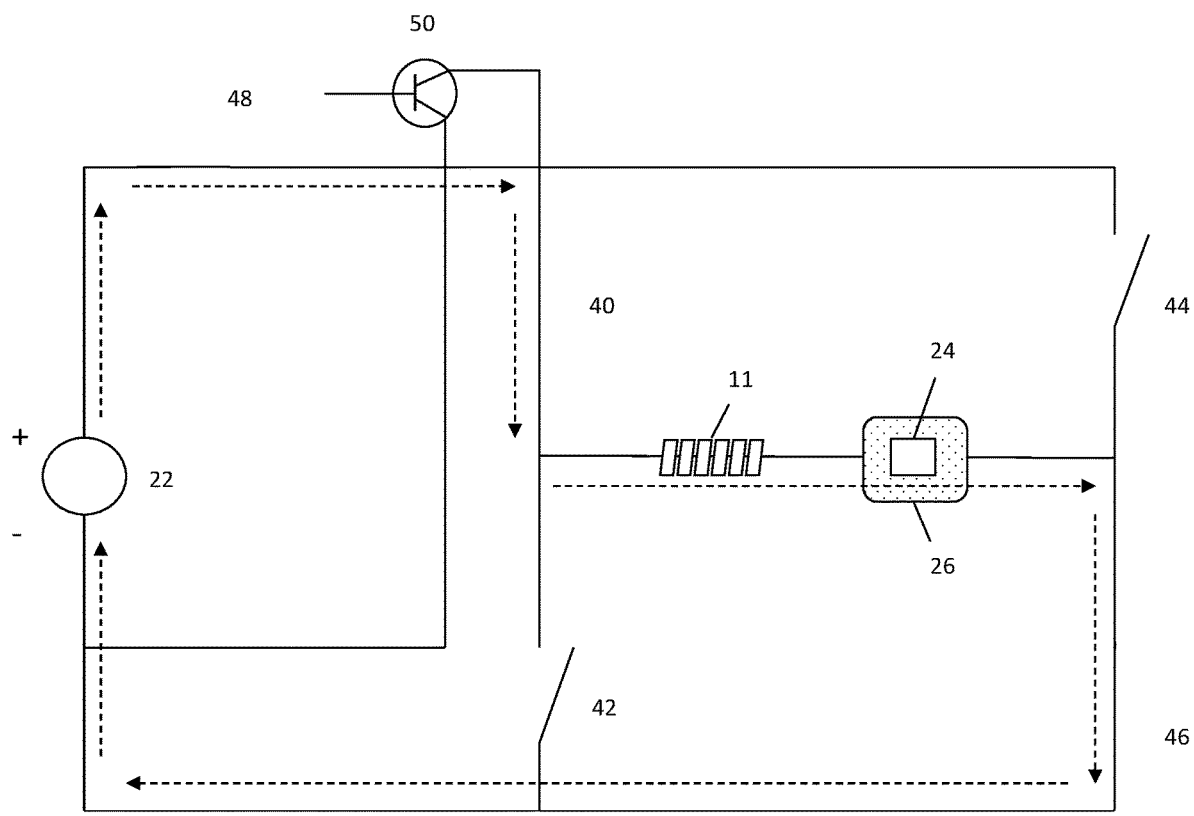

FIG. 11b illustrates a system utilizing pulse width modulation to apply a negative charge to the hydrogel. Switch 48 is in its upper position sending current through transistor 50 which provides pulse width modulation. The current then travels through the skin patch, through the ionic content within the body, through the hydrogel, then back to the negative terminal of the voltage source. This flow path is due to switches 42 and 44 being closed.

FIG. 11c illustrates a system to detach implant 11. Switch 48 is in its lower position, thus avoiding transistor 50 and providing a direct current via the voltage source 22. The current travels through the hydrogel-core wire interface to degrade linkage 30. A user interface could be coupled to the system. These figures are offered as examples of how a pulse-width modulation system could be used in a combined system. The pulse-width system could also be integrated into the systems shown in FIGS. 6-8. Other techniques besides the utilization of a transistor could also be used to provide the pulse-width. In addition to pulse-width, transistor 50 could also be used to provide other current current/voltage delivery options.

In another embodiment transistor 50 could be used to amplify the gain from the voltage source. Where transistor 50 is used to amplify the gain from the voltage source, this amplified gain could be used to detach the implant. Alternatively, where transistor 50 is used to amplify the gain from the voltage source, the amplified gain could be used to provide an electrical stimulus to the hydrogel to cause either expansion or contraction of said hydrogel.

In another embodiment a transistor or other transforming mechanism could be used to decrease the load provided from the voltage source. Where a transistor or other transforming mechanism is used to decrease the load from the voltage source, this decreased load could be used to provide an electrical stimulus to the hydrogel to cause either expansion or contraction of said hydrogel. Alternatively, where a transistor or other transforming mechanism is used to decrease the load from the voltage source, the decreased load could be used to detach the implant.

One system can be used to polarize the hydrogel and another system can be used to detach core wire 28 from implant 11. In one example, the two systems could utilize two separate voltage sources and have separate user interfaces. In another example, the two systems could utilize two separate voltage sources and have a common user interface. Any of the systems shown in FIGS. 6-9 could be used to polarize the hydrogel.

Alternatively, a combined system (such as the one shown in FIGS. 11, 11a-11c) can be used to polarize the hydrogel as well as detach the core wire from the implant. This combined system would utilize the various circuits necessary to accomplish each task and could include a user interface to alternate between the various systems. In one example, this combined system utilizes one voltage source. In one example, different voltages are used to either polarize the hydrogel or detach core wire 28 from implant 11 via degradation of linkage 30. The user may utilize an interface to control these voltage settings. In one example, a circuit utilizing pulse-width modulation is used to control hydrogel expansion or contraction. When detachment is desired, the user can utilize the interface to set another setting whereby a higher voltage setting (i.e. one not utilizing pulse width modulation) would apply an appropriate voltage to the linkage 30 and degrade the linkage from the implant.

Voltage source values can vary based on the properties of the system (i.e. the size of the implant and thus the amount of hydrogel that needs to be polarized). In one example a 9 Volt battery can be used for the systems described above. In another example multiple 9 volt batteries can be used in the systems described having more than one voltage source. In another example multiple 3 Volt batteries can be used for the system/systems described.

Several embodiments are contemplated within the scope of this invention.

In one embodiment, an implant utilizing a hydrogel which can expand and/or contract based on interaction with electricity is described. The implant may utilize a carrier and a hydrogel or the implant may be hydrogel alone.

In another embodiment, systems used to control hydrogel expansion and/or contraction is described. Some of these systems are illustrated in FIGS. 6-9b. Others are described earlier within the specification. As noted earlier, these systems may be combined with other systems or combined with other circuitry (i.e. FIGS. 11-11c) to perform multiple tasks, such as polarizing the hydrogel as well as initiating detachment of the implant from the core wire.

In another embodiment, methods of controlling hydrogel expansion and/or contraction are described. These methods involve applying an appropriate positive charge to the hydrogel to initiate contraction (or mitigate expansion) and applying an appropriate negative charge to the hydrogel to augment expansion. The methods of controlling hydrogel expansion and/or contraction may utilize the systems described earlier.

In another embodiment, methods of utilizing a hydrogel which undergoes expansion and/or contraction via electricity are described. One method may involve using one or more of the systems described earlier to limit expansion of the hydrogel during deployment of the hydrogel within the catheter or delivery device. Another method may utilize the systems described above to limit expansion of the hydrogel within the vasculature until the user wants the hydrogel to expand. At this time the positive charge may be removed and a negative charge (augmenting expansion) may optionally be applied to enhance the space filling potential of the hydrogel. The hydrogel (or hydrogel-containing implant) may be detached from the core wire or delivery pusher upon placement within the vasculature.

In another embodiment a method of utilizing an implant comprising a hydrogel which undergoes expansion and/or contraction via electricity is described. The steps described above could be utilized for an implant which includes a hydrogel. In an example the implants shown in FIGS. 1-2 and 3-5 may be used, where the implant shown in FIGS. 1-2 allow the hydrogel to expand through the carrier and the implant shown in FIGS. 3-5 does not allow the hydrogel to expand through the carrier. The hydrogel-containing implant may be detached from the core wire or delivery pusher upon placement within the vasculature.

Implants utilizing electrically-responsive hydrogels may also be used in a number of scenarios including but not limited to treatment of aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature. In one example, the expansion of hydrogel due to exposure to a negative polarity can be used to cause a hydrogel or hydrogel-containing implant to treat any of the conditions described above. An electrically-responsive hydrogel could also be used as a vessel plug used to plug any of the conditions described above.

Electrically-responsive hydrogels and the systems and methods used to control them could also be useful for a number of other implants and scenarios, besides the ones described earlier. This will be discussed in more depth now.

In another embodiment an electrically-responsive hydrogel is used with a drug delivery device. In one example a drug reservoir may be placed within a hydrogel. When the hydrogel contracts (i.e. upon exposure to a positive charge) the drug will be released. This could be used in an implant utilizing drug delivery (i.e. an embolic coil or stent with drug delivery). In another example the drug reservoir may sit at the periphery of an implant and hydrogel expansion (i.e. upon exposure to a negative charge) may push the drug out, thus releasing it.

In another embodiment an electrically-responsive hydrogel could be used with a catheter (i.e. guide catheter, microcatheter, delivery sheaths, or other delivery devices) to aid in steering or guiding the catheter within the patient vasculature. A hydrogel coating could be placed at the distal tip of the catheter, or at various locations longitudinally along the catheter. The hydrogel could be placed at various locations along the periphery of the catheter, as well. If the catheter is stuck in a particularly tortuous portion of the vasculature, the hydrogel may be polarized (expanded or contracted) to tilt the catheter. If multiple hydrogel sections are placed along the catheter, one or more hydrogel sections can be polarized to manipulate the position of the catheter within the vasculature, thus aiding in tracking and navigating the catheter. This idea could also be used to help track a guidewire within the patient vasculature by coating a guidewire with a hydrogel in one or more locations and selectively expanding/contracting the one or more hydrogel portions to aid in tracking and navigating the guidewire.

In another embodiment a catheter used to deliver liquid embolic may utilize an electrically-responsive hydrogel. Liquid embolic reflux during liquid embolic delivery is a major issue, as the microcatheter delivering the embolic may get stuck to the embolic mass during delivery. A hydrogel ring may be placed near the distal end of the microcatheter. This hydrogel will expand upon contact with blood, but the hydrogel can be negatively polarized to increase its expansion (or speed up the time it takes to fully expand). In one example, upon completion of liquid embolic delivery the microcatheter can be withdrawn and the ring stays with the embolic mass. In another example a positive polarity can be applied to the hydrogel to contract the hydrogel and the microcatheter can be withdrawn along with the hydrogel. This positive polarity can also be used to eliminate the chance of premature expansion of the hydrogel during delivery.

In another embodiment an intrasaccular occlusion device may utilize an electrically-responsive hydrogel. An intrasaccular occlusive device may be used to fill aneurysm or other vascular malformations. One example of an intrasaccular device is a conformable mesh used to fill the space within an aneurysm or malformation. The intrasaccular device may be coated with a hydrogel, or may have a hydrogel within the device. The hydrogel may be coupled to a control system to polarize the hydrogel. In one example, after placement of the intrasaccular device within the malformation the hydrogel can be negatively polarized to augment expansion of the hydrogel and enhance space filling potential. In another example, the hydrogel is positively polarized during deployment to inhibit expansion. The positive charge can be removed (and a negative charge may optionally be used) when hydrogel expansion is desired.

In another embodiment a stroke treatment device may utilize an electrically-responsive hydrogel. Stroke treatment devices generally utilize a mechanism to grasp and remove the clot or thrombus from the vasculature. In one example a hydrogel plug may be used to grasp the clot. The hydrogel plug may be positively polarized to limit expansion during catheter tracking. Upon deployment within the vasculature, this charge can be removed. Alternatively, a negative charge can be utilized to augment plug expansion. The plug can be used to grasp and remove the clot. In one example, upon retention of the clot, the plug can be positively polarized to shrink the plug and allow it to track back through the catheter. In another example a clot retrieval device (i.e. a mechanical system used to physically grasp and remove the clot) may be coated with an electrically-responsive hydrogel to promote attachment between the clot retrieval device and clot/thrombus. The hydrogel may be selectively polarized to effect contraction (i.e. during deployment) and expansion (i.e. upon contact with thrombus).

In another embodiment an anchor within the vasculature may utilize an electrically-responsive hydrogel. It may be desirable to anchor a guidewire within the patient vasculature to stabilize the guidewire in a particular location. A microcatheter or delivery device can then be tracked over this guidewire. A hydrogel can be used at a distal portion of the guidewire. This hydrogel can be selectively polarized. In one example, upon placement at the target location within the vasculature the guidewire is anchored into place via expanding the hydrogel (i.e. by natural exposure to blood or via a negative polarity applied to said hydrogel). Once the microcatheter or delivery device is tracked over said guidewire, the hydrogel may be positively polarized to contract said hydrogel and the guidewire can then be withdrawn.

The various control systems described in FIGS. 6-9b, 11-11c could be utilized with the various electrically-responsive hydrogel-containing devices described earlier (i.e. drug delivery devices, steerable catheters, liquid embolic delivery catheters, intrasaccular occlusion, stroke treatment, anchor, etc.).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of electrically inducing a change in state of a hydrogel of an implant comprising:
   advancing the implant outside of a delivery device; and,
   applying electrical current from a power source connected to the implant, through a patient's body, and through the hydrogel of the implant so as to control contraction and/or expansion of the hydrogel of the implant.

2. The method according to claim 1, wherein applying the electrical current through the hydrogel shrinks or mitigates expansion of the hydrogel.

3. The method according to claim 1, wherein applying the electrical current through the hydrogel expands the hydrogel or augments expansion of the hydrogel.

4. The method according to claim 1, wherein the applying the electrical current includes selectively modulating the pulse width of the electrical current.

5. The method according to claim 1, further comprising disconnecting the implant from the power source.

6. The method according to claim 1, wherein the applying electrical current through the hydrogel is performed after disconnecting the implant from the delivery device.

7. The method according to claim 1, wherein the implant is a helical coil having a hydrogel coating.

8. The method according to claim 1, wherein the implant is a helical coil containing the hydrogel.

9. The method according to claim 1, wherein the medical implant is a slotted tube containing the hydrogel.

10. The method according to claim 1, applying the electrical current further comprises applying electrical current through a patch contacting the patient's body.

11. The method according to claim 1, wherein the implant comprises a carrier in which the hydrogel is held under tension.

12. The method according to claim 1, wherein applying the electrical current comprises adjusting the power source such that the deliver device has a negative polarity or adjusting the power source such that the delivery device has a positive polarity.

13. The method according to claim 1, wherein the power supply is configured to switch polarities so as to expand or shrink the hydrogel.

14. The method according to claim 1, wherein the applying the electrical current is configured to both control contraction and/or expansion of the hydrogel and detach the implant from the delivery device.

15. A method of electrically inducing a change in state of a hydrogel of an implant comprising:

applying electrical current from a power source, through a delivery device, through a implant comprising hydrogel, and through a patient's body, wherein the electrical current controls contraction and/or expansion of the hydrogel of the implant.

16. The method according to claim 15, wherein applying the electrical current 1) shrinks or mitigates expansion of the hydrogel, and/or 2) expands or augments expansion of the hydrogel.

17. The method according to claim 15, wherein the applying the electrical current is preceded by advancing the implant out of the delivery device and detaching the delivery device from the implant.

18. The method according to claim 15, wherein the applying the electrical current includes selectively modulating the pulse width of the electrical current.

19. A method of electrically inducing a change in state of a hydrogel of an implant comprising:
   creating an electrical pathway between a power source, a delivery device, an implant comprising hydrogel, and through a patient's body;
   applying electrical current through the pathway control contraction and/or expansion of the hydrogel of the implant.

\* \* \* \* \*